US011243102B2

(12) United States Patent
Fenn et al.

(10) Patent No.: US 11,243,102 B2
(45) Date of Patent: Feb. 8, 2022

(54) TANK LEVEL AND FLOW RATE MONITORING SYSTEM

(71) Applicant: Absolute Control, LLC, Waller, TX (US)

(72) Inventors: Todd Fenn, Cypress, TX (US); Dave Goodin, Cypress, TX (US); Lou Birdsong, Galveston, TX (US); Brad Fenn, Houston, TX (US); Tom Hendrix, Magnolia, TX (US)

(73) Assignee: ABSOLUTE CONTROL, LLC, Houston, TX (US)

(*) Notice: Subject to any disclaimer, the term of this patent is extended or adjusted under 35 U.S.C. 154(b) by 39 days.

(21) Appl. No.: 15/337,266

(22) Filed: Oct. 28, 2016

(65) Prior Publication Data

US 2017/0227387 A1 Aug. 10, 2017

Related U.S. Application Data

(60) Provisional application No. 62/291,124, filed on Feb. 4, 2016.

(51) Int. Cl.

| | |
|---|---|
| ***G01F 1/00*** | (2006.01) |
| ***G01F 23/00*** | (2006.01) |
| ***G06Q 50/06*** | (2012.01) |
| ***E21B 21/08*** | (2006.01) |

(52) U.S. Cl.

CPC .............. *G01F 1/007* (2013.01); *E21B 21/08* (2013.01); *G01F 23/0061* (2013.01); *G06Q 50/06* (2013.01)

(58) Field of Classification Search

CPC ..... G01F 1/007; G01F 23/0061; G06Q 50/06; E21B 29/00; E21B 21/08

See application file for complete search history.

(56) References Cited

U.S. PATENT DOCUMENTS

| | | | | |
|---|---|---|---|---|
| 4,867,254 | A * | 9/1989 | Gavignet | E21B 21/08 175/48 |
| 2004/0040746 | A1 * | 3/2004 | Niedermayr | E21B 21/08 175/38 |
| 2004/0238177 | A1 * | 12/2004 | Fossli | E21B 21/001 166/364 |
| 2014/0326038 | A1 * | 11/2014 | Fauveau | G01F 25/0061 73/1.73 |
| 2015/0090342 | A1 * | 4/2015 | Cartwright | G05D 9/12 137/2 |
| 2016/0232997 | A1 * | 8/2016 | Kim | G21D 1/00 |
| 2016/0291609 | A1 * | 10/2016 | Lucas | C09K 8/62 |
| 2017/0191350 | A1 * | 7/2017 | Johns | E21B 41/0092 |

OTHER PUBLICATIONS

IOGP, Hydrocarbon process single and multi-layer level measurement recommended practice, Date Dec. 2015, pp. 1-96.*
K-TEK, "MT5100 Guided Wave Radar Level Transmitter K_TEK Products", ABB, pp. 1-48 (Year: 2011).*

* cited by examiner

*Primary Examiner* — Eyob Hagos
(74) *Attorney, Agent, or Firm* — Mackey Law Firm PLLC

(57) ABSTRACT

The embodiments disclosed herein relate to an apparatus for monitoring a fluid level in a returns tank in the oil and gas industry, the apparatus having a sensor configured to monitor the fluid level of the returns tank, wherein the sensor is located within the tank; and a communication device configured to transmit the fluid level from the sensor to a programmable logic controller.

22 Claims, 8 Drawing Sheets

TANK LEVEL AND FLOW RATE MONITORING SYSTEM

STATEMENTS REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND

Technical Field

The subject matter generally relates to techniques for monitoring and managing drilling operations, completion operations and/or production operations at a wellsite, in particular the return rate or flow rate for flow-back and drill out operations in the oil and gas industry. The subject matter further relates to visual aids that may be used by rig operators.

Oilfield operations may be performed in order to extract fluids from the earth. For the duration of the life of a wellsite, an operator may perform various operations in order to extract the fluids. By way of example, the operator may perform drilling operations to form a wellbore; the operator may perform completion operations in order to transform the open wellbore into a wellbore that can safely produce the fluids from the earth; the operator may perform production operations in order to extract the fluids from the earth; and further, any other suitable operations may be performed by the operator. During wellsite completion operations, including, by way of example, during plug drill-out post fracturing well service, the operators must maintain a return rate while plugs are drilled out with a coiled tubing unit or other means. This operation normally requires a constant flow rate of barrels in and barrels out to ensure the removal of solids from the well and to control formation gas that might enter the wellbore. Conventionally, as a part of attempting to maintain a constant flow rate, the operator must evaluate the returns tank and manually determine a current flow rate by “strapping” the tank with a strapping stick, dipstick or tape measure and performing hand calculations based on the rise and conversion to barrels per minute. In doing so, oilfield personnel may be subject to dangerous conditions near the returns tank, which could contain harmful gases, fluids and solids exiting the piping at high velocity, along with other risks these employees will be exposed to in order to obtain the fluid measurement. Additionally, the accuracy of such calculations may also be improved beyond use of the conventional method. Such operations can lead to complexity in managing the efficiency and safety of the wellsite. Therefore, a need exists for a tank level and flow rate monitoring system that enhances the efficiency and the safety of flow-back and drill out operations about the wellsite.

BRIEF SUMMARY

The embodiments disclosed herein relate to an apparatus for monitoring a fluid level in a returns tank in the oil and gas industry, the apparatus having a sensor configured to monitor the fluid level of the returns tank, wherein the sensor is located within the tank; and a communication device configured to transmit the fluid level from the sensor to a remote display and recording device.

BRIEF DESCRIPTION OF THE DRAWINGS

The embodiments may be better understood, and numerous objects, features, and advantages made apparent to those skilled in the art by referencing the accompanying drawings. These drawings are used to illustrate only typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

DETAILED DESCRIPTION OF THE EMBODIMENT(S) SHOWN

The description that follows includes exemplary apparatus, methods, techniques, and instruction sequences that embody techniques of the inventive subject matter. However, it is understood that the described embodiments may be practiced without these specific details.

Figure 1:
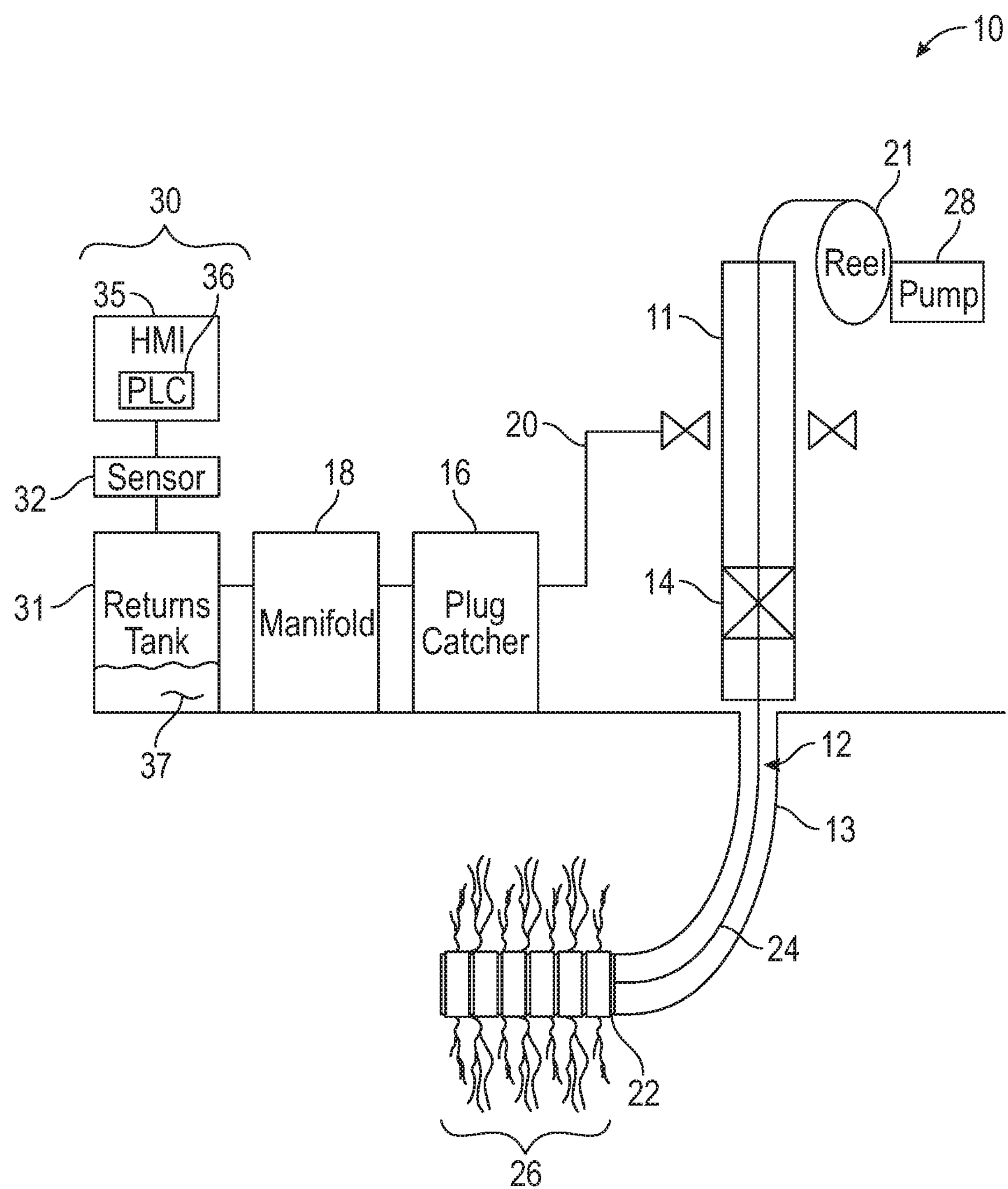
FIG. 1 depicts a schematic diagram of a wellsite having an exemplary embodiment of a tank level and flow rate monitoring system.
Figure 2:
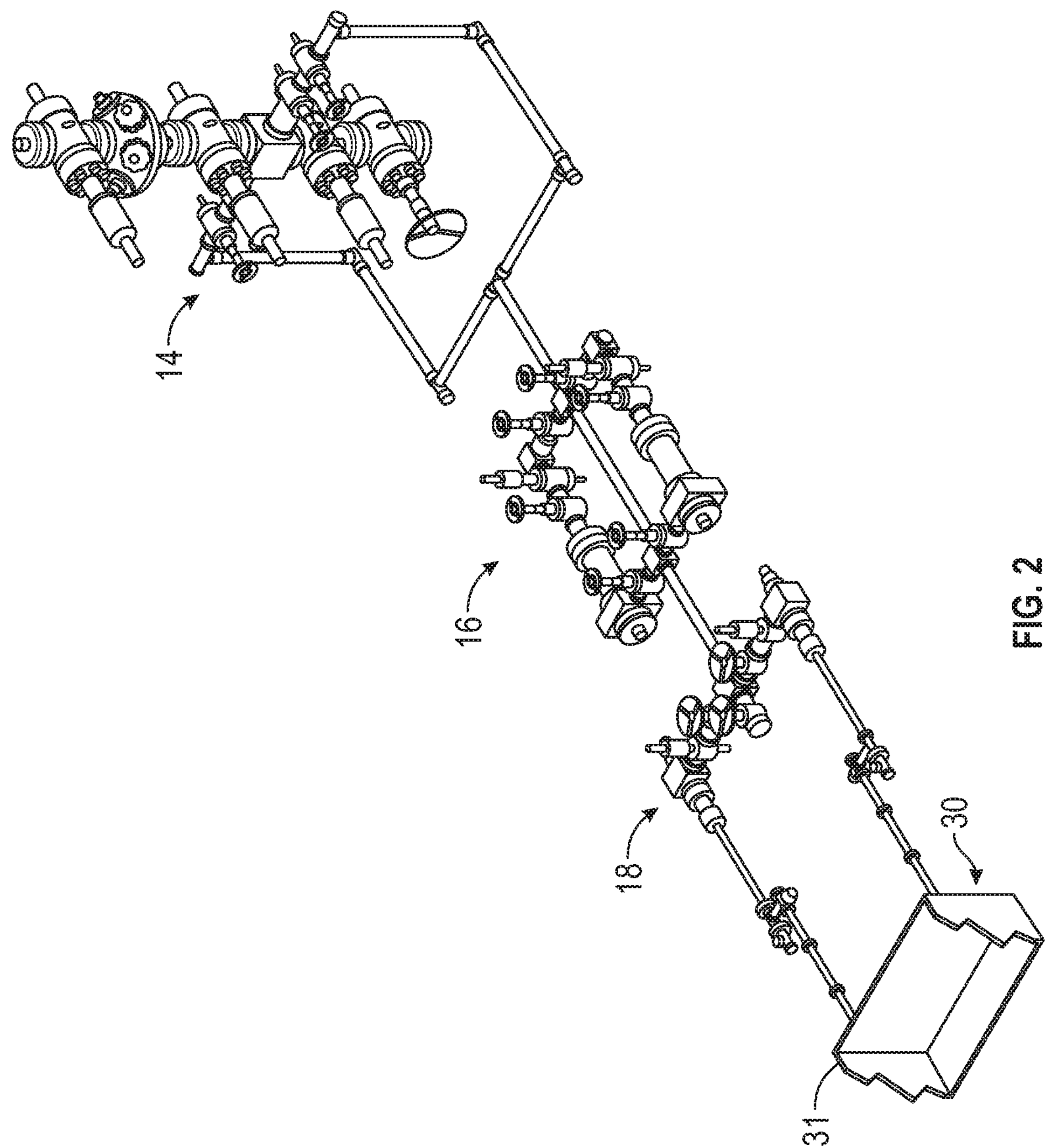
FIG. 2 depicts a perspective view of exemplary embodiments of the well control device, trash catcher, choke manifold and a tank level and flow rate monitoring system.

FIG. 1 depicts a schematic diagram of a wellsite or drill site 10 having an exemplary embodiment of a tank level and flow rate monitoring system, assembly or apparatus 30. FIG. 2 depicts another perspective view of exemplary embodiments of the well control device or devices (also known as a “frac tree”, “well stack” or “frac stack”) 14, a plug, trash or cuttings catcher 16, a choke manifold 18 and a tank level and flow rate monitoring system 30. The drill site or wellsite 10 equipment may include, but is not limited to a drilling rig 11, one or more well control devices 14, a plug or trash catcher 16, a choke manifold 18, a reel or coiled tubing reel 21, a mud pump 28, a drill string and drill bit 24, a returns tank 31 and the like. The returns tank 31 may further recycle the volume of drilling fluid or mud 37 back to the mud pump 28 for re-use in the well bore 12. The wellbore 12 has been formed and a casing 13 has been cemented into place, along with one or more plugs 22 within the well bore 12 in the exemplary embodiment shown in FIG. 1. One or more perforations or fractures 26 may have been formed in a production zone through the casing 13 in order to enhance extraction of the fluids from the wellbore 12. The well site 10 equipment may include a variety of connections, tubing, piping, pipes or hoses 20 to deliver, move or pump a volume of mud or other drilling fluid 37 from one area to of the well site 10 another (such as from the mud pump 28 to the wellbore 12, and subsequently to the well control devices 14, the plug or trash catcher 16, the choke manifold 18 and to the returns tank 31).

The well control devices 14 are used to direct or isolate flow of the fluid 37 from the well head. The plug or trash catcher 16 is used for the purpose of catching solids or debris larger than a predetermined diameter. The choke manifold 18 is used to regulate the flow from the wellhead and/or well control devices 14. The returns tank 31 is used to collect all the fluid 37 returns from the wellbore 12, and is also where the sensor 32 of the tank level and flow rate monitoring system 30 is installed.

Although the depicted well site 10 is a terrestrial system in FIG. 1, it is to be appreciated that the disclosed embodiments may be practiced in alternate environments, including, but not limited to, offshore drilling units as well. Further, it is to be appreciated that the exemplary embodiments disclosed herein may be utilized with any cased or uncased wellbores 12, including any curved, deviated and vertical and horizontal wellbores 12.

During completion phase operations, the drilling mud or fluid 37 is continuously delivered from the mud pump 28 to the drill string and drill bit 24 as the drill 24 drills through the plugs 22 within the well bore 12. As the fluid 37 flows out of the drill 24 into the well bore 12, the fluid 37 carries the cuttings from the plugs 22 (or other debris) back to the surface of the well bore 12, to the well control devices 14 (wherein the fluid 37 is then transferred via connections 20 to the plug or cuttings catcher 16, where the cuttings and debris are retained or caught for removal from the fluid 37). If the fluid 37 is not continuously moving or being pumped into the well bore 12, or kept a desired flow rate, the cuttings or debris will sink further into the well bore 12; however, should the flow rate of the fluid 37 into the well bore 12 exceed the flow rate of the fluid 37 out of the well bore 12, there is also a risk of forcing the fluid 37 into the production zone or the formation and damaging the formation. The drill string can also get stuck if the flow rates of the fluid 37 in and out of the well bore 12 are not appropriately matched.

Figure 3:
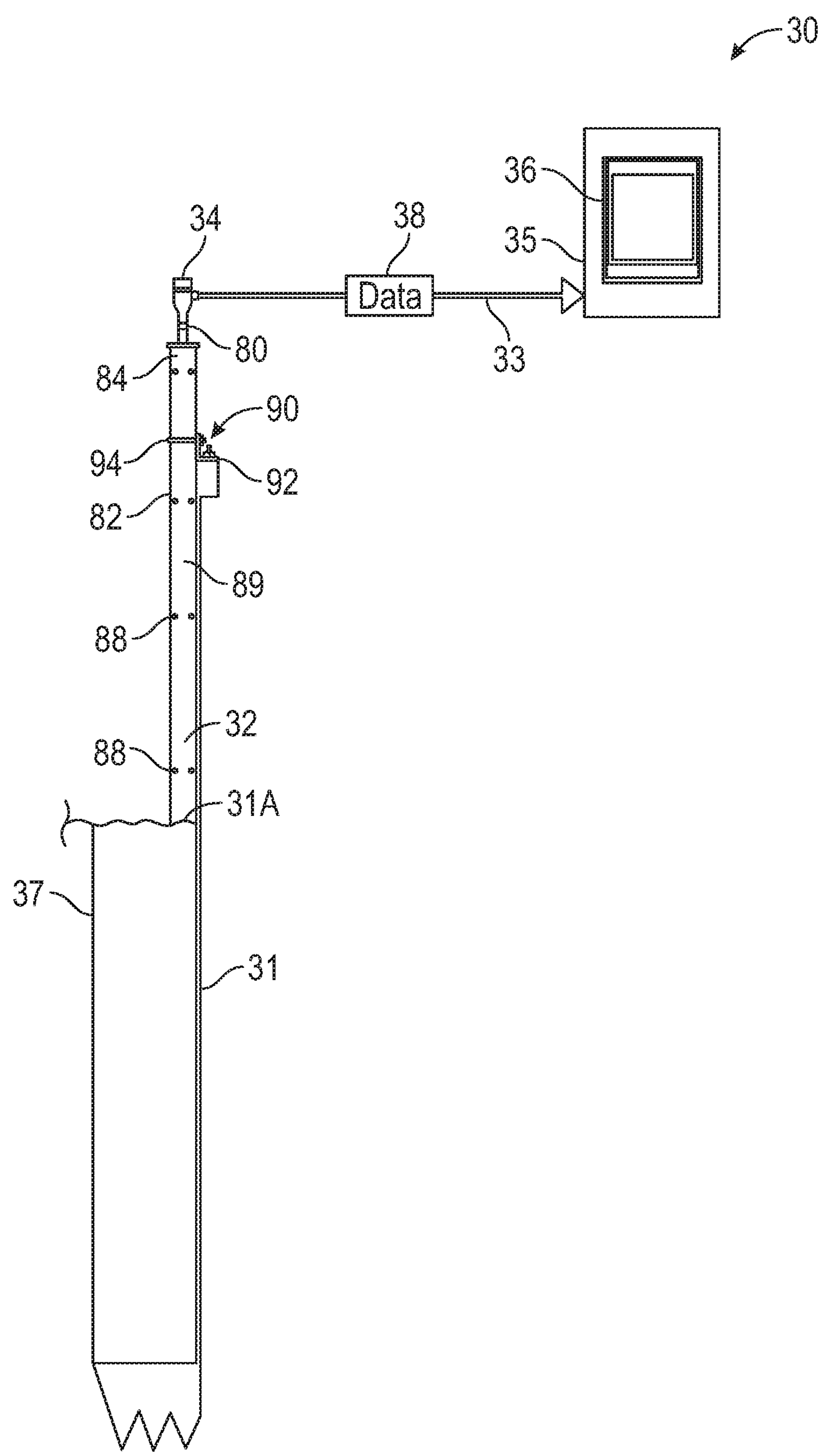
FIG. 3 depicts a partial cross section view of an exemplary embodiment of a tank level and flow rate monitoring system.
Figure 3A:
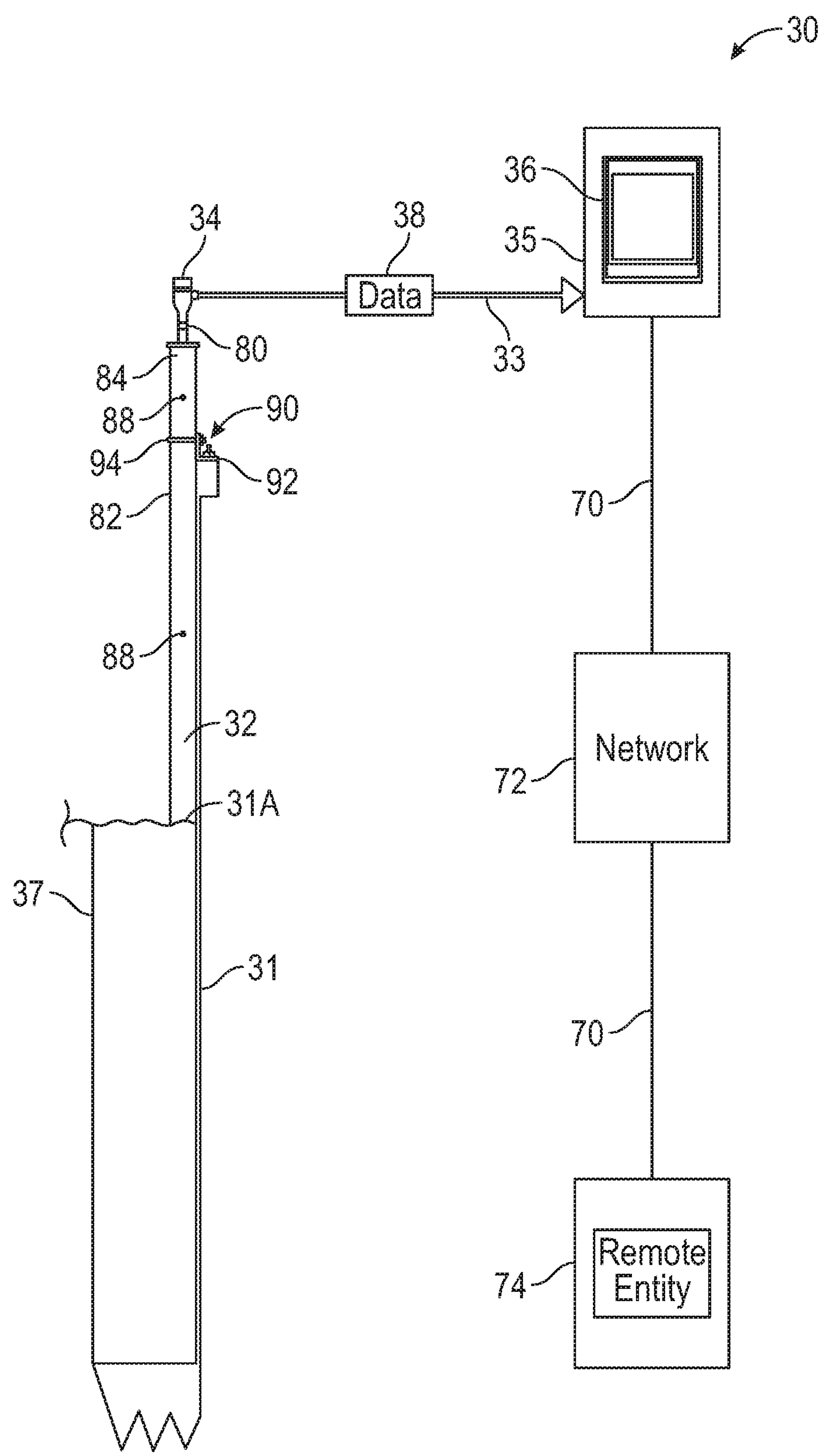
FIG. 3A depicts the exemplary embodiment of FIG. 3 together with a schematic view of one exemplary embodiment of a remote data transmission and fluid level and/or flow rate monitoring system.
Figure 4:
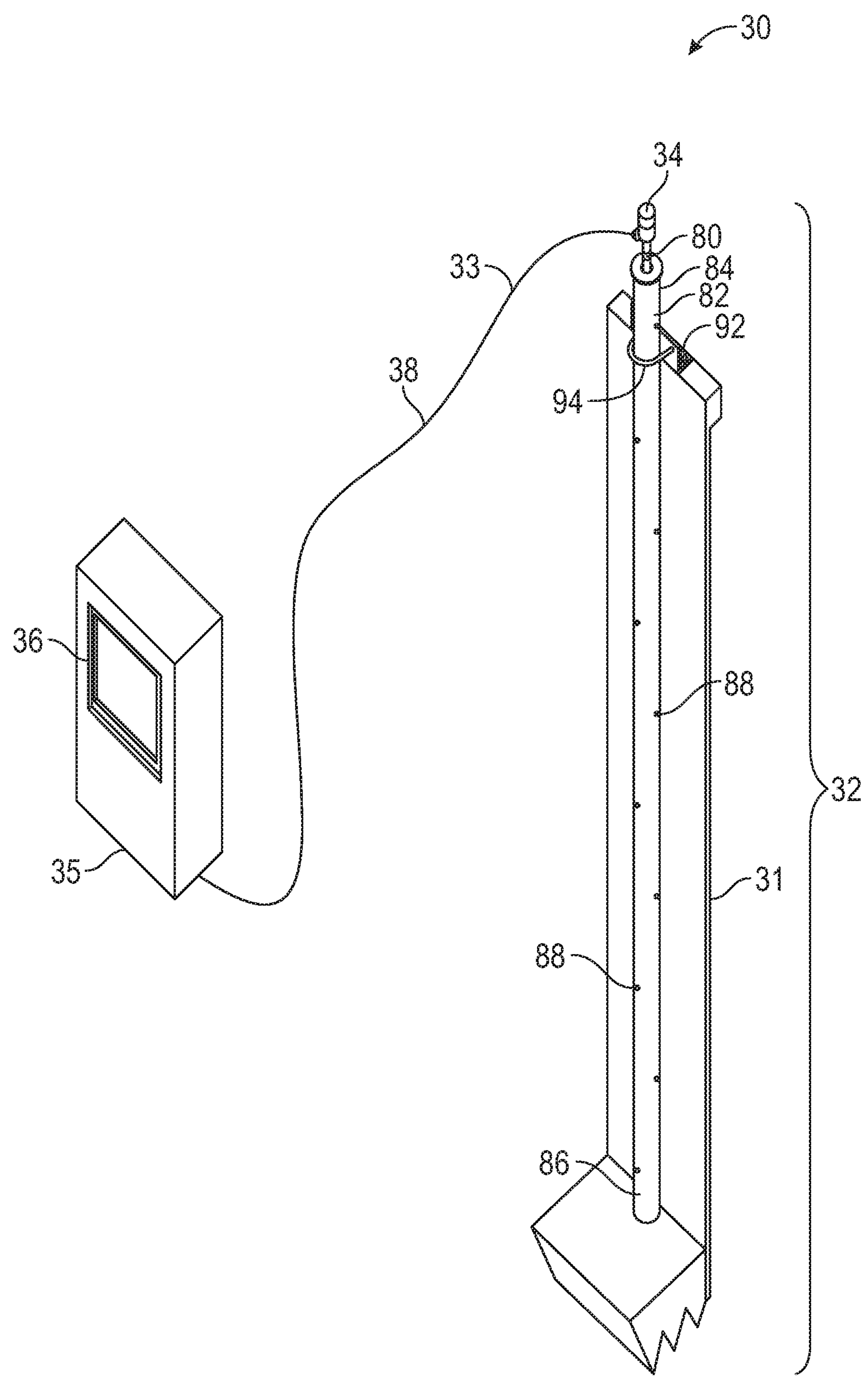
FIG. 4 depicts a perspective and partial cross section view of an alternative exemplary embodiment of a tank level and flow rate monitoring system.

FIG. 3 depicts a partial cross section view of an exemplary embodiment of a tank level and flow rate monitoring system 30 having a transmitter 34 for the data 38. FIG. 4 depicts a partial cross section view of an alternative exemplary embodiment of a tank level and flow rate monitoring system 30, wherein the data 38 is transmitted via cables or wires 33. Further, the communication device or means, even though depicted as a transmitter 34 in FIG. 3 or cables 33 in FIG. 4, in alternative exemplary embodiments, may be any suitable system for relaying data 38 about the wellsite 10. The communication device may include wires, wireless communication, acoustic communication, telemetry tools, and the like. The communication device may be limited to relaying information or data 38 about the tank 31 to the PLC 35. In an alternative exemplary embodiment, the communication device may include an internet, or cloud communication network, that allows a remote entity 74 (see FIG. 3A) to remotely monitor operations about the wellsite 10. The remote entity may have access to a portion of or the entire PLC 35.

Exemplary embodiments of the tank level and flow rate monitoring system 30 may include, but is not limited to, a returns tank or tank 31, one or more computers, electronic modules or programmable logic controllers (hereinafter, also "PLCs") 35, a display interface or human machine interface (hereinafter, also "HMIs") 36, one or more sensors or probes 32, and a communication network (see, for example communication network 72 in FIG. 3A), device or means (by way of example only, a transmitter 34 as shown in FIG. 3 and/or cables or wires 33 as shown in FIG. 4). In certain exemplary embodiments, the PLC 35 and the display 36 may be a standalone unit; in alternative exemplary embodiments, the PLC 35 and the display 36 may be mounted in a separate control unit (not illustrated). Moreover, the PLC 35 and the display 36 may be integrated into a combined assembly. Additionally, the tank level and flow rate monitoring system 30 may have its electrical components powered through a power plug and socket or, in alternative exemplary embodiments, may be powered with a battery. The tank level and flow rate monitoring system 30 collects data 38 about the returns tank 31 and presents it to the drill site operator. Then the operator, with the help of the PLC 35, may make decisions that ensure the performance of safe and efficient operations. The returns tank 31 may be any type of an open top or closed top tank (also known as a "frac tank").

The sensor or probe 32 may collect or gather data 38 in real time as operations are performed about the wellsite 10. The sensor 32 may then send or deliver the collected data 38 to the PLC 35 via a transmitter 34 or cables 33 (or as noted elsewhere, any communication means as known to one of ordinary skill in the art). The sensor or probe 32 may primarily measure the tank level 31*a* (see FIG. 3), but in alternative exemplary embodiments, the sensor 32 (or other additional sensors) may measure any suitable parameter about the tank 31 or drill site 10 and the like. The sensor 32 may be any suitable type of level sensor 80 including, but not limited to magnetostrictive (and other float technologies), radar, guided wave radar, laser, and/or other types of sensors, coupled to a stilling well 82, which can include a first end 84, a second end 86 and a plurality of openings 88 in an exterior surface 89 thereof. The sensor 32 may collect data 38 continuously during the operations and send the data to the PLC 35.

The PLC 35 (which may include an on board computer (s)) may be a traditional desktop computer, or any other suitable computer including, but not limited to, a tablet, a laptop, a personal digital assistant, or any combination of processing, logic, or control units and the like. In one embodiment the PLC 35 may be a commercially available off-the-shelf component. In certain exemplary embodiments, the PLC 35 may also house an internet portal or other data transmitter for transmitting a signal and/or data 70 remotely (see FIG. 3A). The internet portal may communicate the signal or data 70 to a satellite, cellular, Wi-Fi, and/or other communication system/network 72. The communication system/network 72 and internet portal may also be configured to receive data 70, as well as transmit data 70. The communication system/network 72 can transmit or relay a signal and/or data 70 to a remote end user/receiver (which may include a computer or handheld controller) 74

The PLC 35 and/or display interface 36 may include any kind of data input and output devices as known to one of ordinary skill in the art to communicate with a user, including but not limited to, a digital display screen (which may or may not have touch screen recognition), a keyboard, a mouse, switches or buttons, microphones, speakers, and the like. Instructions from the user is entered via the PLC 35 and/or display interface 36 (or remotely) as data 35 and/or 70. The user-input data 35 and/or 70 may be communicated via the internet portal and/or communication system/network 72 to an end user (including a computer) 74. Likewise, data 35 and/or 70 may be received from the transmitter 34, internet portal, communication system/network 72 and/or an end user (including a computer) 74 to be displayed, output, or otherwise communicated to a user via the PLC 35 and/or display interface 36.

Although several data collection systems, methods and/or devices are described it should be appreciated that any suitable data collection systems, methods and/or devices may be used. Part or the entire tank level and flow rate monitoring system 30 may be trailer mounted.

Figure 5:
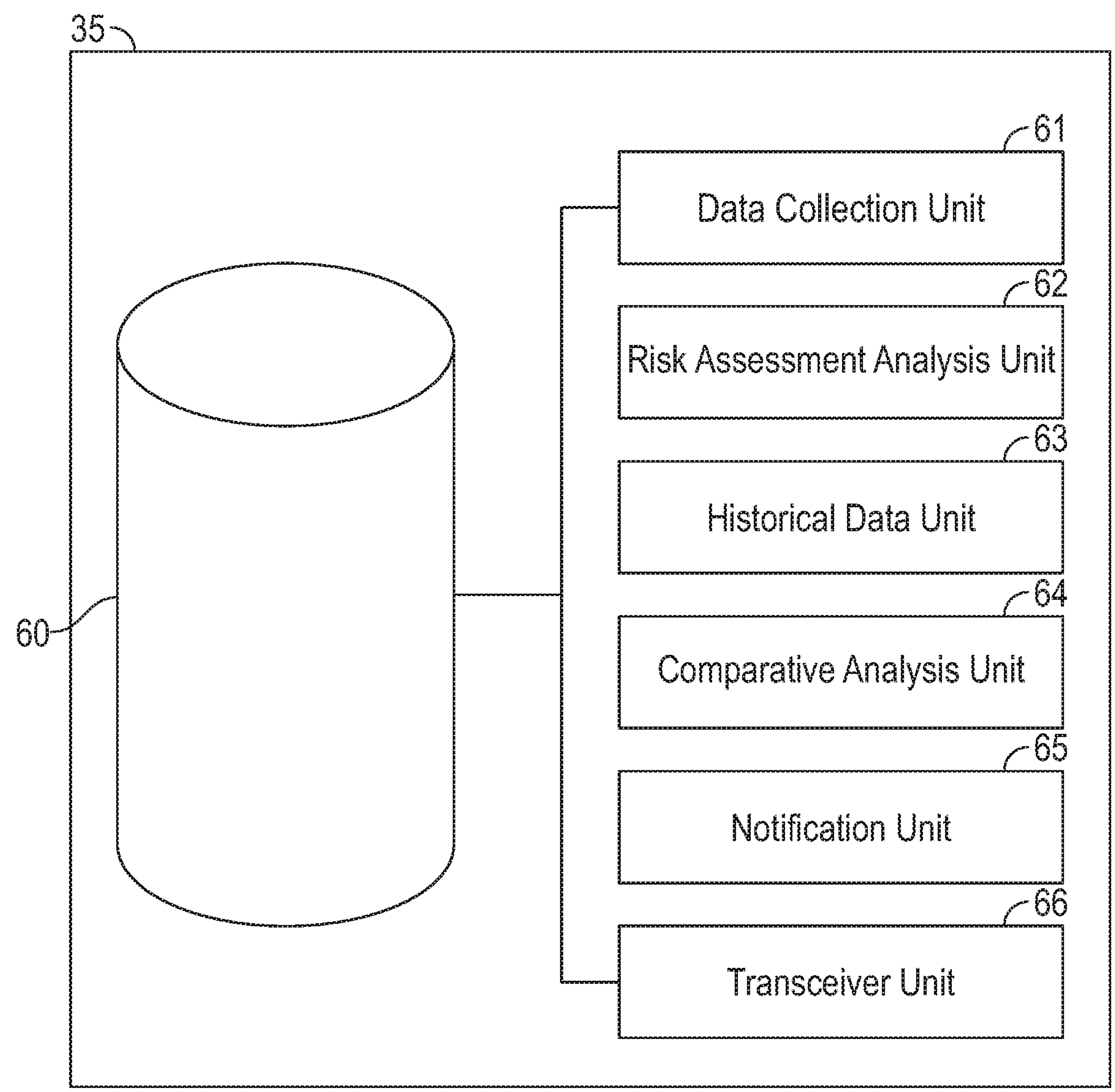
FIG. 5 depicts a schematic diagram of an exemplary embodiment of a programmable logic controller for a tank level and flow rate monitoring system.

FIG. 5 depicts a schematic diagram of an exemplary embodiment of a PLC or programmable logic controller 35 for a tank level and flow rate monitoring system 30. The PLC 35 may have components including, but not limited to, a storage device 60, a data collection unit 61, a risk assessment or analysis unit 62, a historical data unit 63, a comparative analysis unit 64, a notification unit 65, and a transceiver unit 66.

The PLC 35 and its components are generally implemented as electronic circuitry and processor-based computational components controlled by computer instructions stored in physical data storage components 60, including various types of electronic memory and/or mass-storage devices. It should be noted, at the onset, that computer instructions stored in physical data storage devices 60 and executed within processors or microcontrollers 35 comprise the control components of a wide variety of modern devices, machines, and systems, and are as tangible, physical, and real as any other component of a device, machine, or system. Occasionally, statements are encountered that suggest that computer-instruction-implemented control logic is “merely software” or something abstract and less tangible than physical machine components. Those familiar with modern science and technology understand that this is not the case. Computer instructions executed by processors must be physical entities stored in physical devices. Otherwise, the processors would not be able to access and execute the instructions. The term “software” can be applied to a symbolic representation of a program or routine, such as a printout or displayed list of programming-language statements, but such symbolic representations of computer programs are not executed by processors. Instead, processors fetch and execute computer instructions stored in physical states within physical data storage devices 60. Similarly, computer-readable media are physical data storage media 60, such as disks, memories, and mass-storage devices that store data in a tangible, physical form that can be subsequently retrieved from the physical data storage media 60. Moreover, the physical data storage media 60 may optionally be integral with the PLC 35.

Figure 6:
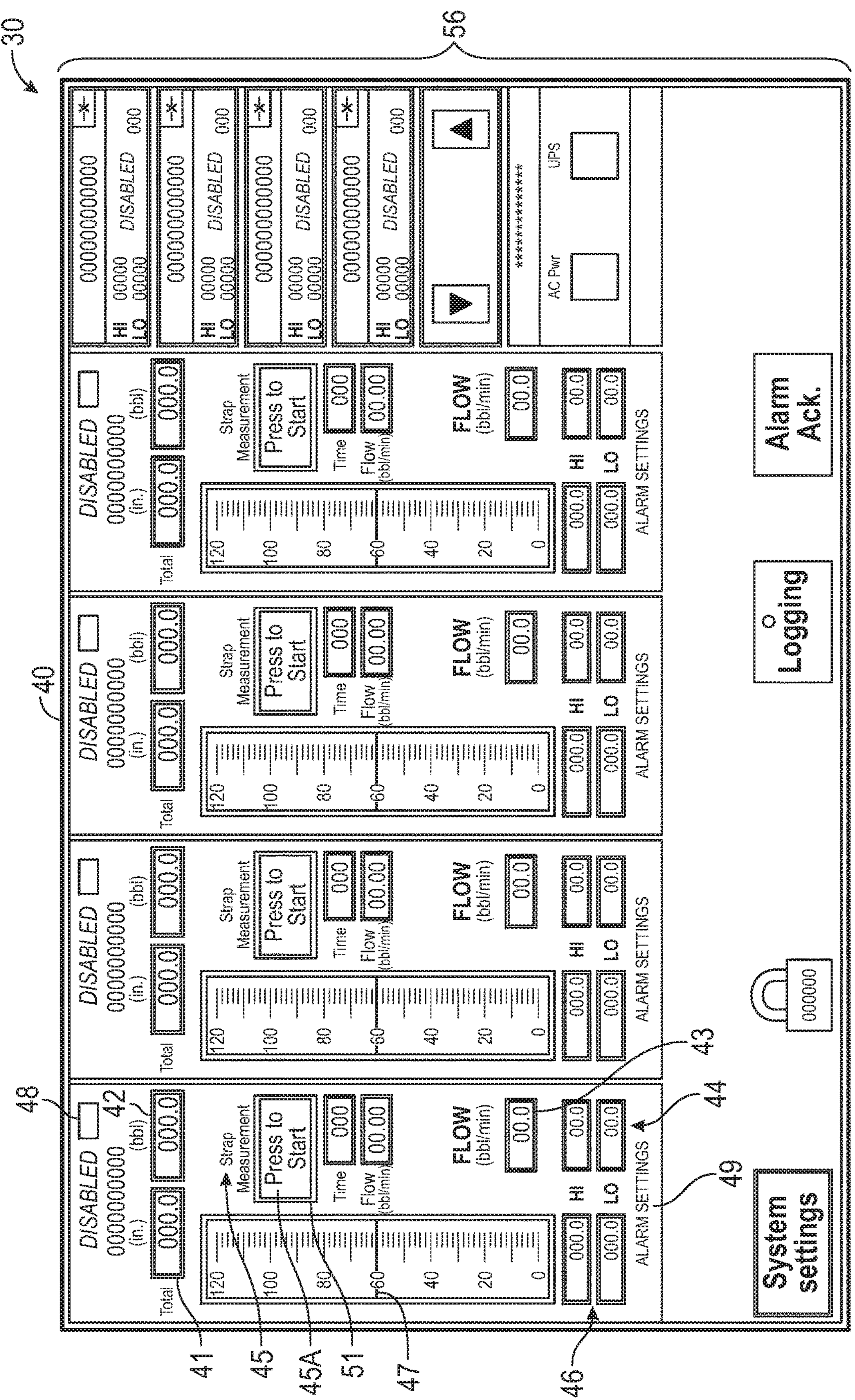
FIG. 6 depicts an exemplary embodiment of a main display for a tank level and flow rate monitoring system.
Figure 7:
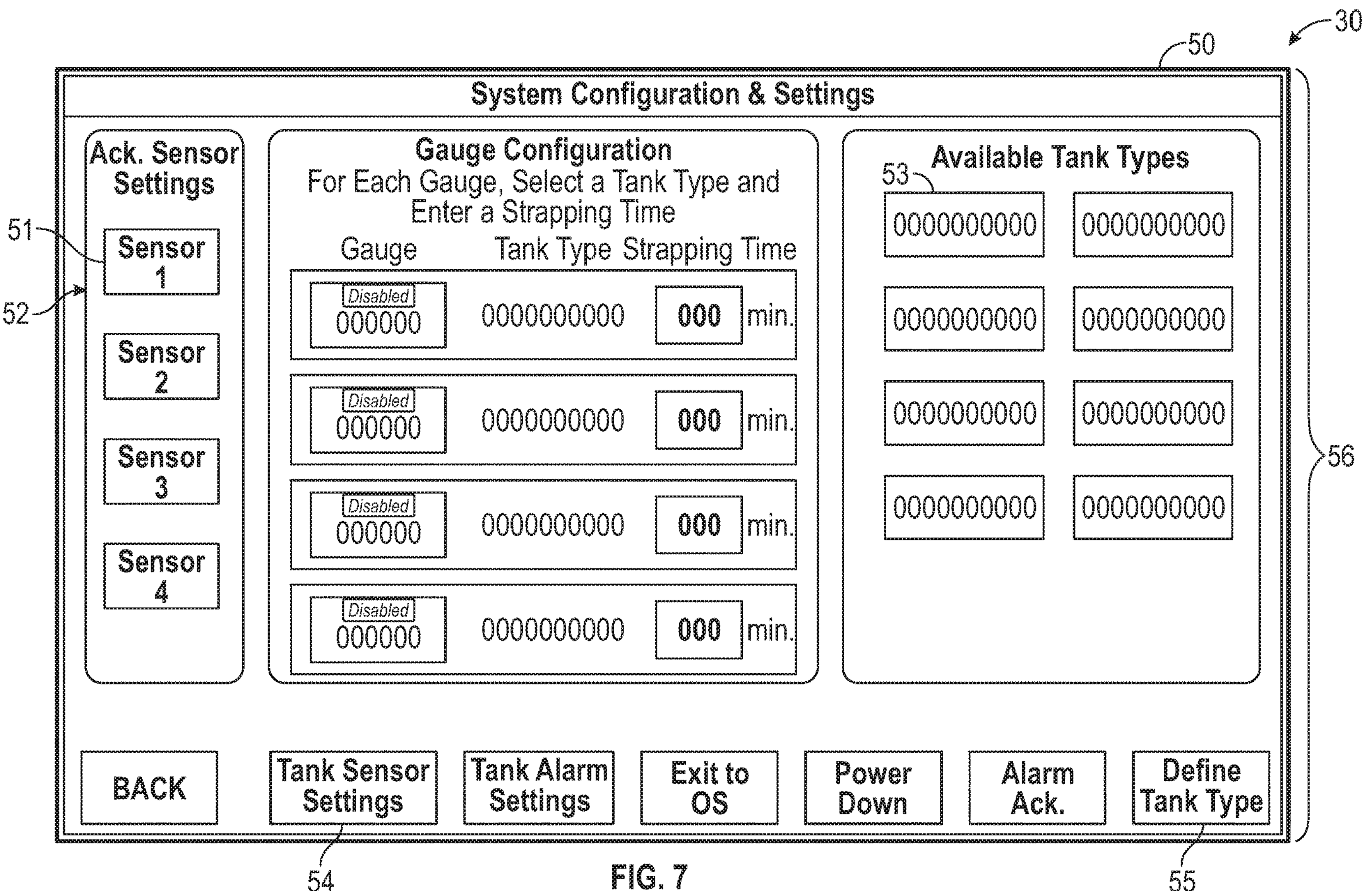
FIG. 7 depicts an exemplary embodiment of a calibration display for a tank level and flow rate monitoring system.

The PLC 35 accesses and uses a variety of different types of stored or received information, signals, feedback, data 38, and inputs 51, including, user/operator input, in order to generate output controls or commands that may trigger or change processes of the PLC 35; such changed processes may include changing the user interfaces or displays 36, including visual and audible alarms 44, 46 as displayed in FIG. 6 and FIG. 7. Received, input or stored information or data 38, whether received to the PLC 35 by user-input or feedback from the sensor 32, includes at least: current measurement of the tank level 31*a*, desired and historic measurements of the tank level 31*a*, and other historical data as recorded or stored by the PLC 35 on a physical data storage media 60, including current, desired and historical calculated flow rate, amongst others. Additional information used by the PLC 35 in its algorithms may include one or more stored control schedules, immediate control inputs received through a control or display interface 36, and data, commands, commissioning, and other information received from remote data-processing systems, including cloud-based data-processing systems (not illustrated). Further, in alternative exemplary embodiments, the PLC 35 may monitor and coordinate data feedback and/or input for the tank 31 to automatically adjust the volume of mud 37 by manipulating the pump 28 (or other well site 10 components, such as the choke manifold 18) to maintain a constant flow rate of mud 37 in and out of the wellbore 12, as based on the measurements or saved data for the tank 31. By way of example only, the PLC 35 may monitor and record the tank level 31*a* over several periods of time into the physical data storage component 60, and adjust the flow rate or amount accordingly to allow for a constant level mud 37 flow input and output throughout the well site 10 life. This history and data 38 stored by the physical data storage component 60 may be further used to troubleshoot, maintain, and repair the components of the well site 10 by the operator or manufacturer of the system, or by the PLC 35 itself. In addition to optionally generating control output to manipulate the components of the well site 10, the PLC 35 also provides a LED, graphic or display interface 36 that allows users/operators to easily input controls for input entries 51 as depicted in FIG. 7 and may also provide output and information to remote entities 74, other microcontrollers, and to users through an information-output interface. In this manner, the PLC 35 may act as a mechanism to sense or receive feedback to adjust and correct the drill site 10 system(s).

Embodiments of the technology may take the form of an entirely hardware embodiment, an entirely software embodiment (including firmware, resident software, micro-code, etc.) or an embodiment combining software and hardware aspects that may all generally be referred to herein as a “circuit,” “module” or “system.” Furthermore, embodiments of the disclosed subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computer system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium; optical storage medium; magneto-optical storage medium; read only memory; random access memory; erasable programmable memory; flash memory; or other types of medium suitable for storing electronic instructions. In addition, the various embodiments may be embodied in an electrical, optical, acoustical or other form of propagated signal (e.g., carrier waves, infrared signals, digital signals, etc.), or wire line, wireless, or other communications medium.

Computer program code for carrying out operations of the embodiments may be written in any combination of one or more programming languages. The program code may execute entirely on a user’s computer, partly on the user’s computer, as a stand-alone software package, partly on the user’s computer and partly on a remote computer or entirely on the remote computer or server by, for example, a remote end user 74. In the latter scenario, the remote computer may be connected to the user's computer through any type of network, including a local area network (LAN), a personal area network (PAN), or a wide area network (WAN), or the connection may be made to an external computer (for example, through the Internet using an Internet Service Provider).

The storage device 60 may be any suitable storage device for storing data. The data collection unit 61 may collect, gather, manipulate, and/or categorize the data 38 collected by the sensor 32 about the tank 31. The data collection unit 61 may manipulate the collected data into a format that allows the operator and/or the PLC 35 to take appropriate action during the operations. The risk assessment or analysis unit 62 may receive the categorized data 38 from the data collection unit 61 in order to determine if there is any present or future risk likely at the well site 10. The risk may be based on real time events that are taking place in the operations and/or based on predictive events that are likely to occur. The risk assessment or analysis unit 62 may classify the risks for the PLC 35 and/or the operator (such as whether to create an alert or alarm 44 or 46 via the notification unit 65). The historical data unit 63 may categorize the historical data 38 collected by the data collection unit 61. The comparative analysis unit 64 may compare the data 38 collected by the data collection unit 61, the classified risks, and/or the historical data 38 in order to determine a course of action for the operator and/or PLC 35. The comparative analysis unit 64 may further determine a flow rate and/or if the tanks level 31*a* or flow rate (or other parameters) is within a predetermined set of parameter values. The tank 31 parameters may be any suitable parameters set by the service company, the client, or any other suitable source or algorithm. The comparative analysis unit 64 may make a determination of how serious the risk is based on the data 38 collected. The comparative analysis unit 64 may relay information to the notification unit 65 so that the notification unit 65 may alert the operator and/or take action. The notification unit 65 may alert the operator or PLC 35 of a real time condition, and/or a predicted condition about the tank 31. The notification unit 65 may include the visual display interface(s) 36, audible sounds or alarms, a kinetic or automated response, and/or a combination thereof. The transceiver unit 66 and/or the transmitter 34 may be any suitable device configured to send and/or receive data to the PLC 35.

In another example, the operator and/or the PLC 35 may update the tank 31 parameters, and/or data 38 as operations are being performed. The operator and/or the PLC 35 could notify or update the historical data unit 63 of any conditions, or parameters, that need to be compared in the future.

FIG. 6 depicts an exemplary embodiment of a main display 40 for a tank level and flow rate monitoring system 30. FIG. 7 depicts an exemplary embodiment of a calibration display 50 for a tank level and flow rate monitoring system 30. The display or interface 36 of the tank level and flow rate monitoring system 30 may include many different display or output screens, including, in an exemplary embodiment, one of a main display 40 and on a different screen or display, a calibration display 50. Each display 36 may include various output display features or information 56, and various user input or entry features 51.

The main display 40 may act as a visual summary for the current status and various parameters of the tank 31 and the tank level 31*a*. The main display 40 in one example may be created and displayed by the PLC 35, and/or any portion of the PLC 35. In alternative embodiments, the main display 40 may allow the operator to view a fraction or all of the data 38 collected that relates to the current real time operations. The main display 40 may be a combination of the current location and projected averages based on the current trends and historical information. The main display 40 is a quick management tool that may show the operator a current status of a parameter, where the status is trending, and/or how fast the operation is trending in that direction. The main display 40 may have any combination of display features 56 to allow the operator to easily read and access the data 38 with a quick view. For example, the display features 56 on the main display 40 may include, but are not limited to, displayed gauges, charts, graphs, logs, any combination thereof, and the like. The main display 40 gives the operator all the management tools for quick informed decisions.

The main display 40 may include a panel or section 49 for each tank 31 under the monitoring of the system 30. Each section 49 may display similar information 56 with another section 49, and may include, by way of example only, a tank level display in inches 41, a tank level display in barrels 42, a display for flow rate (or return rate) in barrels per minute 43, a display for high and low rate alarms 44, a display for a timed strap 45 (including an input button 45*a* to engage or disengage the timed strap 45), a display for a high and low tank level alarm 46, a display of an analog indication of the tank level 31*a* in inches (or other measurement standard), and a display of the sensor diagnostics 48. The display of the sensor diagnostics 48 may serve to indicate whether a sensor 32 is unplugged, or whether one or more communication cables 33 are broken. The visual alarms 44, 46 quickly inform the operator if the operator is operating outside the tank level 31*a* or tank 31 flow rate parameters, and/or approaching the limits of the parameters. Other kinds of alarms (including audible and/or kinetic) may be utilized as described above for the same parameters as set for the visual display alarms 44, 46.

The calibration display 50 may include a plurality of entry or input features 51 including, but not limited to: an input feature to assign a tank and duration for a timed strap 52, an input feature to select and name saved tanks 53, an input feature for sensor calibration 54, and an input feature for tank information entry 55.

To begin initial monitoring, a tank level and flow rate monitoring system 30 is installed at the returns tank 31, such as with a mount 90 including a bracket 92 and a coupler 94. The operator may interact or engage with the calibration screen 50 to calibrate, set or store the data 38 for a specific tank 31. The operator may select and enter label or name for a tank 31 under the entry or input feature 53 by pressing, engaging or otherwise inputting information onto the HMI display 36 or directly into the PLC 35 (by way of example, this may include other commonly known input devices not illustrated in the figures, such as keyboards or mice). Other entries or input areas 51 for data 38 may include an input area for assigning tanks and entering durations for the timed strap 52; an input area for calibrating the level sensor 54; and an input area for defining tank information 55. The entered data 38 may be stored into the PLC 35 components for later access, including one or more of the following components: the storage device 60, the data collection unit 61, the risk assessment and analysis unit 62, the historical data unit 63, the comparative analysis unit 64, the notification unit 65, and/or the transceiver unit 66.

After calibration, monitoring may begin by instructing, commanding or directing the level sensor 32 to begin gathering tank level 31*a* data for a particular tank 31. The instructions may come from a schedule or instructions from one or more components stored in the PLC 35, or from a user or the operator pressing or engaging the timed strap button display feature 45*a* on the main display 40. When directed to begin, the sensor 32 measures or determines a tank level 31*a* at a first time instance, and sends the data 38 of such to the PLC 35 through cables 34 or the transmitter 33. The PLC 35 may display the tank level 31*a* at such time instance on the HMI or display 36, in particular through any or all of the display features or indicators 56 for the tank level in inches 41, for the tank level in barrels 42, and/or the analog gauge display of the tank level in inches 47. Additionally, while the figures depict some of the display features 56 in imperial units (or inches), it is to be appreciated that other units of measurement appropriate to communicate information regarding fluid level or height may be utilized, as is known in the art (such as, by way of example only, and not limited to: metric, e.g., meters, millimeters, and so on). Furthermore, the PLC 35 may store or allocate this data 38 into one or more of the following: the storage device 60, the data collection unit 61, the risk assessment and analysis unit 62, the historical data unit 63, the comparative analysis unit 64, the notification unit 65, and/or the transceiver unit 66.

Subsequently, after a duration of time (difference in time or time difference) as determined by the calibration data, the PLC 35 stored data and/or the operator input, the sensor 32 may determine the tank level 31*a* at a second time instance and report the data 38 of such to the PLC 35. The PLC 35 may also transmit this data 38 to the HMI display 36 to reflect the real-time or current status of the tank level 31*a* and store said data 38 accordingly. Incorporating the volume of the tank 31, and the change, if any, in height of the tank level 31*a*, and the time difference or duration between the two time instances, the PLC 35 may calculate or determine a present or current flow rate of the fluid 37 into the returns tank 31. This data 38 regarding the flow rate may be displayed on the HMI 36 via the display feature for the flow rate in barrels per minute 43. The flow rate data 38 may also be stored or allocated into one or more of the following of the PLC unit 35: the storage device 60, the data collection unit 61, the risk assessment and analysis unit 62, the historical data unit 63, the comparative analysis unit 64, the notification unit 65, and/or the transceiver unit 66. These processes may be conducted in real-time or instantaneously.

In particular, when the PLC 35 has incoming data 38 from the sensor 32 regarding the present tank level 31*a*, the PLC 35 may compare the current measured tank level 31*a* (by way of example, in the comparative analysis unit 64) with historical data or stored data regarding safe or desired ranges for the tank level 31*a*, to determine whether the high low level alarm display 46 needs to alert the operator or a remote entity/user 74 of a potential undesirable situation. If the PLC 35 determines that the tank level 31*a* is beyond the historical or stored data range on safe tank levels, then the PLC 35 may notify the display unit 36 via the notification unit 65 or transceiver unit 66 to update the alarm display 46 accordingly.

Likewise, when the PLC 35 has determined a present flow rate into the returns tank 31, the PLC 35 may compare the current calculated flow rate with historical data or stored data regarding safe or desired ranges for flow rate, to determine whether the high low flow rate alarm display 44 should be communicated to the operator or a remote entity 74 of a potential undesirable situation. If the PLC 35 determines that the present flow rate is beyond the historical or stored data range on safe or desired flow rates, then the PLC 35 may notify the display unit 36 via the notification unit 65 or transceiver unit 66 to update the alarm display 44 accordingly.

Furthermore, should the sensor 32 or the transmitter 34 or cables/wires 33 experience technical difficulties, the PLC 35 may note, record, and alert the situation to the operator via the sensor diagnostics display 48 of the HMI display 36.

While the exemplary embodiments are described with reference to various implementations and exploitations, it will be understood that these exemplary embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

The invention claimed is:

1. An apparatus for monitoring a fluid level in a returns tank in the oil and gas industry, comprising:
- a sensor configured to monitor the fluid level of the returns tank, wherein the sensor comprises a level sensor coupled to a stilling well that is configured to be disposed at least partially within the returns tank;
- a communication device comprising a transmitter configured to transmit fluid level data from the sensor to a programmable logic controller; and
- a mount configured to couple the stilling well to the returns tank;

wherein the stilling well comprises
- a tubular body having a first end configured to be disposed above the fluid level in the returns tank and a second end longitudinally opposite the first end;
- topmost and bottommost openings through a wall of the body that are configured to allow returns fluid flow; and
- a first plurality of interim openings through the wall of the body, the first plurality of interim openings being longitudinally spaced along the body between the first and second ends;
- wherein the mount is configured to couple to a top edge of the returns tank, above the fluid level, and is attached to the stilling well above the topmost opening through the wall of the body.

2. The apparatus of claim 1, further comprising a communication network in data communication with the programmable logic controller and with a remote end user system, wherein the programmable logic controller is configured to communicate fluid level data received from the transmitter to a receiver of the remote end user system via the communication network.

3. The apparatus of claim 1, further comprising:
- a data collection unit configured to collect data from the sensor;
- a comparative analysis unit configured to determine if the fluid level of the returns tank and/or a flow rate into the returns tank is within a predetermined set of parameter values; and
- a notification unit configured to alert an operator based on the determination of the comparative analysis unit.

4. The apparatus of claim 1, wherein the level sensor is coupled to the first end of the stilling well.

5. The apparatus of claim 1, wherein the transmitter is coupled to the first end of the stilling well.

6. The apparatus of claim 1, further comprising a second plurality of interim openings through the wall of the body of the stilling well, wherein the second plurality of interim openings is longitudinally spaced along the body and transverse to the first plurality of interim openings.

7. The apparatus of claim 2, further comprising a first display in data communication with the programmable logic controller and a second display in data communication with the remote end user system, wherein each of the first and second displays is configured to display at least a portion of the fluid level data.

8. The apparatus of claim 1, further comprising a non-transitory computer readable medium stored within or accessible by the programmable logic controller and having instructions stored thereon that, when executed by a processor, cause the processor to perform a method comprising:

sensing a first fluid level of the returns tank at a first time instance with the level sensor;

communicating the first fluid level to the programmable logic controller and recording the first time instance in the programmable logic controller;

sensing a second fluid level of the returns tank at a second time instance with the level sensor;

communicating the second fluid level to the programmable logic controller and recording the second time instance in the programmable logic controller; and determining a flow rate into the returns tank based on a time difference between the first time instance and the second time instance and a difference between the first fluid level and the second fluid level.

9. The apparatus of claim 8, wherein the instructions cause the processor to perform a method further comprising:

categorizing historical fluid level data, the historical fluid level data comprising at least one of sensed fluid levels, time instances, flow rates and a combination thereof;

comparing historical fluid level data to other fluid level data; and determining whether a risk exists that a flow rate or tank level will deviate from a set of parameter values.

10. The apparatus of claim 9, wherein the instructions cause the processor to perform a method further comprising:

determining that a risk exists that a flow rate or tank level will deviate from a set of parameter values;

determining whether to create an alarm based on the risk; and notifying an operator of the risk by creating at least one of a visual alarm, an audible alarm and a combination thereof.

11. The apparatus of claim 1, further comprising:

a first display in data communication with the programmable logic controller; and a non-transitory computer readable medium stored within or accessible by the programmable logic controller and having instructions stored thereon that, when executed by a processor, cause the processor to perform a method comprising visually displaying, on the first display, a first panel of information that corresponds to the returns tank, wherein the first panel of information includes tank level in units of length, tank level in units of volume and flow rate for the first returns tank.

12. The apparatus of claim 11, further comprising a remote entity in data communication with the programmable logic controller, wherein the remote entity comprises a second display that visually displays the same information as the first display.

13. The apparatus of claim 11, wherein the instructions cause the processor to perform a method further comprising visually displaying, on the first display, a plurality of panels of information that each corresponds to a corresponding one of a plurality of returns tanks, wherein each of the plurality of panels of information includes tank level in units of length, tank level in units of volume and flow rate for its corresponding returns tank.

14. The apparatus of claim 1, further comprising:

a first display in data communication with the programmable logic controller; and a non-transitory computer readable medium stored within or accessible by the programmable logic controller and having instructions stored thereon that, when executed by a processor, cause the processor to perform a method comprising visually displaying, on the first display, a button for starting a strap measurement at least partially carried out by the sensor;

in response to engagement of the button, measuring a first fluid level at a first time instance;

after a duration of time, measuring a second fluid level at a second time instance;

determining a flow rate based on the first and second fluid levels and the first and second time instances; and visually displaying the flow rate on the first display.

15. The apparatus of claim 14, wherein the instructions cause the processor to perform a method further comprising obtaining the duration of time from calibration data stored within or accessible by the programmable logic controller.

16. The apparatus of claim 1, wherein the mount supports the body of the stilling well without the need for additional mounts.

17. The apparatus of claim 1, wherein a portion of the mount is configured to extend inwardly over an open top of the returns tank and to hold the body of the stilling well vertically and at least partially within the returns tank.

18. The apparatus of claim 1, wherein the body of the stilling well is suspended into an open top of the returns tank from the mount.

19. The apparatus of claim 1, wherein the body of the stilling well hangs along an interior wall of the returns tank from the mount.

20. The apparatus of claim 1, wherein the returns fluid comprises drilling mud returned from a wellbore.

21. A system for monitoring a fluid level in a returns tank, comprising:

a sensor comprising a level sensor coupled to a stilling well;

a mount including a bracket coupled to the stilling well and configured to couple the sensor to the returns tank;

a transmitter coupled in data communication with the sensor and a programmable logic controller; and a display coupled in data communication with the programmable logic controller;

wherein the stilling well comprises a tubular body having a first end and a second end longitudinally opposite the first end;

topmost and bottommost openings through a wall of the body that are configured to allow returns fluid flow; and a first plurality of interim openings through the wall of the body, the first plurality of interim openings being longitudinally spaced along the body between the topmost and bottommost openings;

wherein the stilling well is configured to be disposed at least partially within the returns tank in a vertical orientation with the first end above the fluid level in the returns tank;

wherein the mount is configured to couple to a top edge of the returns tank, above the fluid level, and is attached to the stilling well above the topmost opening through the wall of the body;

wherein the level sensor is configured to measure a fluid level of the returns tank; and further comprising a non-transitory computer readable medium stored within or accessible by the programmable logic controller and having instructions stored thereon that, when executed by a processor, cause the processor to perform a method comprising sensing a first fluid level at a first time instance with the level sensor;

communicating the first fluid level and the first time instance to the programmable logic controller;

sensing a second fluid level at a second time instance with the level sensor;

communicating the second fluid level and the second time instance to the programmable logic controller;

determining a flow rate based on a difference between the first time instance and the second time instance and a difference between the first fluid level and the second fluid level; and visually displaying, on the display, a panel of information that includes the flow rate determined.

22. The system of claim 21, wherein the level sensor and the transmitter are coupled to the first end of the stilling well, and wherein the second end of the stilling well is configured to be disposed within the returns tank vertically below the first end of the stilling well.

* * * * *